United States Patent [19]

Reilly

[11] 4,257,968

[45] Mar. 24, 1981

[54] OXIDATION OF PHENOL TO P-BENZOQUINONE IN ACETONITRILE/METHANOL COSOLVENT

[75] Inventor: Edward L. Reilly, Wilmington, Del.

[73] Assignee: E. I. Du Pont de Nemours and Company, Wilmington, Del.

[21] Appl. No.: 81,806

[22] Filed: Oct. 4, 1979

[51] Int. Cl.³ ............................................ C07C 46/08
[52] U.S. Cl. ............................................... 260/396 R
[58] Field of Search ................................... 260/396 R

[56] References Cited

U.S. PATENT DOCUMENTS

| | | | |
|---|---|---|---|
| 3,870,731 | 5/1975 | Hutchings | 260/396 |
| 3,987,068 | 10/1976 | Reilly | 260/396 |

*Primary Examiner*—Vivian Garner

[57] ABSTRACT

An improved process for making p-benzoquinone by contacting phenol with an oxidant in the presence of a copper salt catalyst, the improvement which comprises employing a cosolvent system of acetonitrile and methanol, the weight ratio of acetonitrile to methanol being about 1 to 20:1.

9 Claims, No Drawings

OXIDATION OF PHENOL TO P-BENZOQUINONE IN ACETONITRILE/METHANOL COSOLVENT

BACKGROUND OF THE INVENTION

1. Field of the Invention

The process of this invention is related to that claimed in U.S. Pat. No. 3,987,068 and filed in Class 260/396 R.

2. Description of the Prior Art

P-benzoquinone is an intermediate in the formation of hydroquinones which are useful as antioxidants, reducing agents, polymer intermediates, etc.

U.S. Pat. No. 3,987,068 concerns a process for making p-benzoquinone wherein phenol is contacted with a source of oxygen in the presence of a copper salt catalyst in a nitrile solvent such as acetonitrile. The patent contains no suggestion of an acetonitrile/methanol cosolvent system.

U.S. Pat. No. 3,210,384 teaches the making of a tetrasubstituted dibenzoquinone by oxidizing disubstituted phenol in the presence of a copper salt catalyst in a solvent comprising acetonitrile. Cosolvents such as methanol, ethanol, acetone, trichloroethylene, etc., can be employed "providing they do not interfere or enter into the oxidation reaction" (column 6, lines 49 and 50).

U.S. Pat. No. 3,870,731 teaches the oxidation of phenol to p-benzoquinone in the presence of copper salt catalysts, a catalyst promoter, and methanol. The patent does not disclose acetonitrile solvent.

U.S. Pat. No. 3,859,317 teaches the cobalt and manganese-catalyzed oxidation of phenol to p-benzoquinone in the presence of a solvent such as methanol. Acetonitrile is not disclosed.

There is nothing in the prior art to suggest the improvement in yield and productivity made possible by employing the specific acetonitrile/methanol cosolvent system described herein.

SUMMARY OF THE INVENTION

This invention concerns an improvement in the process for making p-benzoquinone (quinone),

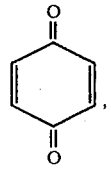

from phenol,

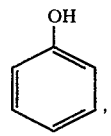

and an oxidant in the presence of a copper salt catalyst. The improvement comprises employing a cosolvent system comprising acetonitrile and methanol, the weight ratio of acetonitrile to methanol being about 1 to 20:1. The preferred ratio of acetonitrile to methanol is 2 to 10:1.

The oxidant can be oxygen, or, preferably, an oxygen-containing gas. The reaction is carried out under pressure, the partial pressure of oxygen being about 10 to 100 atmospheres (1.0 to 10.1 MPa). Reaction temperatures are normally about 20° to 80° C.

The copper salt catalysts can be one or more salts selected from the group consisting of cuprous chloride, cuprous bromide, and cupric chloride.

The term "consumption" employed herein is defined as the number of moles of phenol that went into the reaction minus the number of moles that came out of the reaction, divided by the number of moles in; said fraction multiplied by 100. "Consumption" is a measure of the percent of starting phenol used up.

The term "yield" which is a measure of the selectivity and efficiency of the process of this invention is defined as the number of moles of quinone produced, divided by the consumption; said fraction multiplied by 100.

The term "productivity" is defined for a continuous reactor at steady state as the number of gram moles of benzoquinone (BQ) produced per hour, divided by the number of liters of liquid reaction mixture in the reactor, g moles/L-hr.

DETAILS OF THE INVENTION

An oxygen partial pressure of about 1.0 to 10.1 MPa will insure that the reaction is directed toward production of p-benzoquinone and away from production of polymeric products. Typically, an acetonitrile/methanol solution of phenol and copper salt catalyst is contacted with air, oxygen, or oxygen diluted with any other gas which does not interfere with the reaction. When air is used as the oxidizing agent, air pressures of about 5 to 50 MPa, preferably 7 to 35 MPa, are employed. CAUTION SHOULD BE EXERCISED WHEN THE OXIDANT IS UNDILUTED OXYGEN.

The amount of copper salt used should be sufficient to provide a ratio of about 5 to 25 moles of the phenol per mole of copper salt. With higher molar ratios, the amount of copper salt is so small that the phenol consumption, as well as the amount thereof converted to the benzoquinone drops. No advantage in terms of yield is achieved in using an amount of copper salt in excess of that which gives about a 5/1 molar ratio of phenol to copper salt.

The concentration of the acetonitrile/methanol solution of the phenol can vary widely. There is no minimum concentration to be adhered to except that which is dictated by practical considerations. At concentrations of about 50% or more of phenol based on the weight of the acetonitrile/methanol, the phenol consumption tends to decrease. Therefore, a preferred concentration range is about 10% to 50%. The molar ratio of solvent to copper salt is in excess of about 10/1, and often in excess of about 100/1.

The solution of the phenol in the solvent containing the copper complex is contacted with the oxidant for about 10 minutes or more, the specific time required in any given case depending on the reaction temperature and the molar ratio of phenol to copper salt. There is no advantage to reaction times exceeding about two hours.

The following Examples illustrate various embodiments of the invention.

EXAMPLES 1 TO 11 AND COMPARISONS A TO C

Batch Operation

The general procedure utilized for the batch runs was as follows. Phenol and catalyst were dissolved in acetonitrile/methanol cosolvent in a Hastelloy "C" reactor. The reactor was then pressurized with air and heated with agitation. The reactor was then cooled to about room temperature and vented. Specific conditions and results are noted in Table 1.

TABLE 1

[Reaction time: 1 hour; 10 grams of phenol in 50-60 mL of acetonitrile/methanol; all runs employed air at 2000 psig (13.8 MPa)].

| Ex. or Comp. | Catalyst | Wt. of Catalyst | Wt. percent of Methanol | Temp. °C. | Phenol Consumption (Percent) | Yield of BQ (Percent) |
|---|---|---|---|---|---|---|
| 1 | CuCl$_2$·2H$_2$O/CuCl | 0.85/0.50 | 20 | 50 | 61 | 59 |
| 2 | CuCl$_2$·2H$_2$O/CuCl | 1.15/0.35 | 20 | 50 | 57 | 65 |
| 3 | CuCl$_2$·2H$_2$O/CuCl | 0.85/0.50 | 33 | 50 | 45 | 62 |
| 4 | CuCl$_2$·2H$_2$O/CuCl | 1.15/0.35 | 33 | 50 | 40 | 65 |
| 5 | CuCl$_2$·2H$_2$O | 1.7 | 20 | 40 | 36 | 42 |
| 6 | CuCl$_2$·2H$_2$O | 1.7 | 20 | 50 | 48 | 75 |
| 7 | CuCl | 1.0 | 20 | 60 | 88 | 61 |
| 8 | CuCl$_2$·2H$_2$O | 1.7 | 17 | 50 | 62 | 71 |
| 9 | CuCl$_2$·2H$_2$O | | | 50 | 57 | 74 |
| 10 | CuCl$_2$·2H$_2$O | 1.7 | 50 | 50 | 49 | 59 |
| 11 | CuCl | 1.0 | 50 | 50 | 60 | 62 |
| A | CuCl$_2$·2H$_2$O | 1.7 | 100 | 50 | 15 | — |
| B | CuCl$_2$·2H$_2$O | 1.7 | 0 | 50 | 76 | 53 |
| C | CuCl | 1.0 | 0 | 50 | 84 | 48 |

EXAMPLES 12 TO 63 AND COMPARISONS D TO G

Continuous Operation

In continuous operation of the present process, a solution of phenol and copper salt catalyst in acetonitrile/methanol and an oxidant were fed continuously into a stirred tank reactor. Product solution was removed continuously from the reactor.

Tables 2 to 4 summarize a number of continuous runs in acetonitrile/methanol, i.e., according to the process of this invention. In addition, a number of runs are summarized of comparative processes, i.e., wherein no methanol cosolvent was employed. The Comparative Examples serve to highlight the benefits that flow from the process of this invention.

In these Tables, "Short" holdup times are about 0.25 hr, "Medium" holdup times are about 0.40 hr, and "Long" holdup times are about 0.80 hour. "Holdup time" is defined as liters of liquid reaction mixture in the reactor, divided by the liquid feed rate in liters per hour. Pressures given are air pressures. Catalyst concentrations vary from 0.1 to 0.3 g mole per liter of feed as indicated.

Comparison of the continuous operation of the process employing cosolvent vs. the process employing only acetonitrile (and no cosolvent) demonstrates an increase in yield of up to about 20% and an increase in productivity of up to about 15% for the cosolvent process of this invention.

TABLE 2

[Air Oxidation; 60° C.; 20.7 MPa; 0.10 g mol of CuCl and 1.06 g mol of phenol per liter of phenol/solvent/catalyst feed]

| Ex. or Comp. | Cosolvent Used | Wt. Percent Cosolvent | Holdup Time | Phenol Consumption (Percent) | BQ Yield, (Percent) | Productivity g moles/L-hr |
|---|---|---|---|---|---|---|
| D | None | — | Long | 74.8 | 53.9 | 0.57 |
| 12 | MeOH | 21.7 | Long | 68.5 | 66.1 | 0.63 |
| 13 | MeOH | 21.7 | Long | 46.9 | 78.7 | 0.53 |
| E | None | — | Medium | 61.0 | 56.6 | 0.90 |
| 14 | MeOH | 21.7 | Medium | 57.0 | 66.7 | 1.05 |
| 15 | MeOH | 21.7 | Short | 45.9 | 66.8 | 1.24 |

TABLE 2A

[Same conditions as in Table 2 except 2.13 g mole of phenol per liter of feed]

| Ex. | Cosolvent Used | Wt. Percent Cosolvent | Holdup Time | Phenol Consumption (Percent) | BQ Yield, (Percent) | Productivity g moles/L-hr |
|---|---|---|---|---|---|---|
| 16 | MeOH | 21.7 | Long | 45.3 | 49.0 | 0.60 |
| 17 | MeOH | 21.7 | Long | 34.0 | 77.8 | 0.76 |
| 18 | MeOH | 21.7 | Medium | 40.0 | 42.5 | 0.96 |
| 19 | MeOH | 21.7 | Short | 22.9 | 39.7 | 0.78 |

TABLE 3

[Air oxidation, 60° C.; 20.7 MPa; 0.20 g mole of CuCl and 1.06 g mole of phenol per liter of phenol/solvent/catalyst feed]

| Ex. or Comp. | Cosolvent Used | Wt. Percent Cosolvent | Holdup Time | Phenol Consumption (Percent) | BQ Yield, (Percent) | Productivity g moles/L-hr |
|---|---|---|---|---|---|---|
| 20 | MeOH | 21.7 | Long | 59.6 | 70.2 | 0.60 |
| 21 | MeOH | 21.7 | Long | 87.2 | 61.9 | 0.73 |
| F | None | — | Medium | 81.5 | 46.8 | 1.01 |
| 22 | MeOH | 21.7 | Medium | 70.4 | 62.2 | 1.14 |
| 23 | MeOH | 21.7 | Medium | 68.2 | 61.0 | 1.16 |
| G | None | — | Short | 81.6 | 43.2 | 1.50 |
| 24 | MeOH | 21.7 | Short | 60.8 | 57.6 | 1.60 |
| 25 | MeOH | 21.7 | Short | 60.1 | 54.7 | 1.50 |

TABLE 3A

[Same conditions as in Table 3 except 2.13 g mole of phenol per liter of feed]

| Ex. | Cosolvent Used | Wt. Percent Cosolvent | Holdup Time | Phenol Consumption (Percent) | BQ Yield, (Percent) | Productivity g moles/L-hr |
|---|---|---|---|---|---|---|
| 26 | MeOH | 21.7 | Long | 52.3 | 82.8 | 1.23 |
| 27 | MeOH | 21.7 | Long | 60.6 | 74.5 | 1.31 |
| 28 | MeOH | 21.7 | Long | 63.1 | 63.0 | 1.13 |
| 29 | MeOH | 21.7 | Medium | 49.4 | 59.7 | 1.55 |
| 30 | MeOH | 21.7 | Short | 48.1 | 44.5 | 1.80 |

TABLE 4

[Air oxidation; 60° C.; 20.7 MPa; 0.30 g mole of CuCl and 1.06 g mole of phenol per liter of phenol/solvent/catalyst feed]

| Ex. | Co-solvent Used | Wt. Percent Co-solvent | Holdup Time | Phenol Consumption (Percent) | BQ Yield, (Percent) | Productivity g moles/L-hr |
|---|---|---|---|---|---|---|
| 31 | MeOH | 21.7 | Short | 66.4 | 52.7 | 1.31 |
| 32 | MeOH | 21.7 | Medium | 71.9 | 60.9 | 1.21 |

TABLES 5 TO 8

Table 5 summarizes additional runs employing acetonitrile/methanol cosolvent at pressures of 34.5 MPa. Table 6 shows that the most preferred process conditions have methanol concentrations in the range of about 10 to 22 weight percent at short and medium holdup times. Table 7 explores the effect of varying temperatures on the process of this invention. Table 8 explores the use of cupric chloride, cuprous bromide and cuprous chloride.

TABLE 5

[Air oxidation, 21.7 weight percent of methanol, 60° C., 34.5 MPa]

| Ex. | CuCl (g Mol/Liter) | Phenol (g Mol/Liter) | Holdup Time | Phenol Consumption (Percent) | BQ Yield (Percent) | Productivity g moles/L-hr |
|---|---|---|---|---|---|---|
| 33 | 0.10 | 1.06 | Long | 61.2 | 71.6 | 0.60 |
| 34 | 0.20 | 1.06 | Medium | 73.2 | 56.8 | 1.17 |
| 35 | 0.20 | 1.06 | Medium | 73.0 | 62.1 | 1.11 |
| 36 | 0.20 | 1.06 | Short | 60.1 | 71.7 | 1.72 |
| 37 | 0.20 | 1.06 | Short | 65.6 | 59.0 | 1.64 |
| 38 | 0.20 | 2.13 | Long | 65.8 | 68.0 | 1.27 |

TABLE 6

[Varying methanol concentrations; 60° C.; Pressures of 34.5 MPa for Examples 39 to 44 and 20.7 MPa for Examples 45 to 47]

| Ex. | CuCl (g Mol/Liter) | Phenol (g Mol/Liter) | Hold-up Time | Wt Percent MeOH | Phenol Consumption (Percent) | BQ Yield (Percent) | Productivity g moles/L-hr |
|---|---|---|---|---|---|---|---|
| 39 | 0.20 | 1.06 | Short | 10.9 | 73.0 | 55.7 | 1.65 |
| 40 | 0.20 | 1.06 | Short | 21.7 | 65.6 | 59.0 | 1.64 |
| 41 | 0.20 | 1.06 | Short | 43.4 | 61.5 | 50.9 | 1.28 |
| 42 | 0.20 | 1.06 | Medium | 10.9 | 78.0 | 66.1 | 1.37 |
| 43 | 0.20 | 1.06 | Medium | 21.7 | 73.2 | 56.8 | 1.17 |
| 44 | 0.20 | 1.06 | Medium | 43.4 | 68.8 | 48.7 | 0.92 |
| 45 | 0.10 | 2.13 | Long | 5.5 | 48.3 | 49.5 | 0.62 |
| 46 | 0.10 | 2.13 | Long | 10.9 | 43.3 | 48.2 | 0.59 |
| 47 | 0.10 | 2.13 | Long | 21.7 | 45.3 | 49.0 | 0.60 |

TABLE 7

[Varying temperature; 21.7 weight percent of methanol; pressures of 34.5 MPa for Examples 48 to 53 and 20.7 MPa for Examples 54 to 56]

| Ex. | CuCl (g Mol/Liter) | Phenol (g Mol/Liter) | Hold-up Time | Temp. °C. | Phenol Consumption (Percent) | BQ Yield (Percent) | Productivity g moles/L-hr |
|---|---|---|---|---|---|---|---|
| 48 | 0.20 | 1.06 | Medium | 40 | 47.5 | 66.1 | 0.92 |
| 49 | 0.20 | 1.06 | Medium | 60 | 73.2 | 56.8 | 1.17 |
| 50 | 0.20 | 1.06 | Medium | 70 | 81.4 | 64.6 | 1.42 |
| 51 | 0.20 | 1.06 | Short | 40 | 44.6 | 68.8 | 1.25 |
| 52 | 0.20 | 1.06 | Short | 60 | 65.6 | 59.0 | 1.64 |
| 53 | 0.20 | 1.06 | Short | 70 | 76.4 | 58.2 | 1.88 |
| 54 | 0.10 | 2.13 | Long | 25 | 13.8 | 85.9 | 0.33 |
| 55 | 0.10 | 2.13 | Long | 60 | 45.3 | 49.0 | 0.60 |
| 56 | 0.10 | 2.13 | Long | 80 | 59.0 | 49.0 | 0.76 |

TABLE 8

| Ex. | Variable | Phenol Consumption (Percent) | BQ Yield (Percent) | Productivity g moles/L-hr |
|---|---|---|---|---|
| | [CuBr vs. CuCl as catalyst at 60° C.; 0.20 g mole of Cu per liter; 1.06 g mol of phenol per liter; 21.7 weight percent of MeOH; long holdup time] | | | |
| 57 | CuBr (34.5 MPa) | 69.2 | 50.3 | 0.51 |
| 58 | CuCl (20.7 MPa) | 59.6 | 70.2 | 0.60 |
| 59 | CuCl (20.7 MPa) | 87.2 | 61.9 | 0.73 |
| | [CuBr vs. CuCl at 60° C.; 0.10 g mol of Cu per liter; 1.06 g mol of phenol per liter; 21.7 weight percent of MeOH, long holdup time; 34.5 MPa] | | | |
| 60 | CuBr | 37.7 | 56.1 | 0.29 |
| 61 | CuCl | 61.2 | 71.6 | 0.60 |
| | [$CuCl_2 \cdot 2H_2O$ vs. CuCl at 60° C.; 0.10 g mol of Cu per liter; 1.06 g mol of phenol per liter; 21.7 weight percent of MeOH; medium holdup time; 20.7 MPa] | | | |
| 62 | $CuCl_2 \cdot 2H_2O$ | 34.6 | 69.7 | 0.61 |
| 63 | CuCl | 57.0 | 66.7 | 1.05 |

The embodiments of the invention in which an exclusive property or privilege is claimed are defined as follows:

1. In a process for making p-benzoquinone by contacting phenol and oxygen or an oxygen containing gas in the presence of a copper salt catalyst, the improvement which comprises contacting the phenol, the oxidant, and the catalyst in the presence of a cosolvent system of acetonitrile and methanol, the weight ratio of acetonitrile to methanol being about 1 to 20:1.

2. The process of claim 1 wherein the catalyst is selected from one or more salts consisting of cuprous chloride, cuprous bromide, and cupric chloride.

3. The process of claim 1 wherein the oxidant is air or oxygen.

4. The process of claim 1 wherein the weight ratio of acetonitrile to methanol is about 2 to 10:1.

5. The process of claim 2 wherein the catalyst is selected from one or more copper salts consisting of cuprous chloride, cuprous bromide, and cupric chloride.

6. The process of claim 5 wherein the oxidant is air supplied at a pressure of about 7 to 35 MPa.

7. The process of claim 6 wherein the catalyst is cuprous chloride.

8. Process of claim 4 wherein the concentration of phenol based upon the weight of cosolvent is in the range 10–50%.

9. The process of claim 8 wherein the oxygen partial pressure is in the range 1.0 to 10.1 MPa.

* * * * *

UNITED STATES PATENT OFFICE
CERTIFICATE OF CORRECTION

PATENT NO. : 4,257,968
DATED : March 24, 1981
INVENTOR(S) : Edward L. Reilly

It is certified that error appears in the above-identified patent and that said Letters Patent are hereby corrected as shown below:

Column 6, line 56, change "2" to -- 4 --.

Signed and Sealed this

Sixth Day of October 1981

[SEAL]

Attest:

GERALD J. MOSSINGHOFF

Attesting Officer    Commissioner of Patents and Trademarks